United States Patent [19]

Jackson et al.

[11] 4,034,418

[45] July 12, 1977

[54] ARTIFICIAL KNEE JOINT

[75] Inventors: Robert W. Jackson; Frederick P. Dewar; David L. MacIntosh; John P. Kostuik; Robin Black, all of Toronto, Canada

[73] Assignee: The Governing Council of the University of Toronto, Toronto, Canada

[21] Appl. No.: 685,379

[22] Filed: May 11, 1976

[30] Foreign Application Priority Data

May 26, 1975 Canada .............................. 227803

[51] Int. Cl.² .......................................... A61F 1/24
[52] U.S. Cl. ..................... 3/1.911; 128/92 C
[58] Field of Search ........................ 3/1, 1.9–1.911; 128/92 C

[56] References Cited

U.S. PATENT DOCUMENTS

| 3,852,830 | 12/1974 | Marmor | 3/1.911 |
| 3,869,731 | 3/1975 | Waugh et al. | 3/1.911 |
| 3,949,428 | 4/1976 | Cavendish et al. | 3/1.911 |
| 3,953,899 | 5/1976 | Charnley | 3/1.911 |

Primary Examiner—Ronald L. Frinks
Attorney, Agent, or Firm—Hirons & Rogers

[57] ABSTRACT

An artificial knee joint for surgical implantation into a knee comprises at least one femoral member of hard plastic material and at least one tibial member having a highly polished metal upper surface. The femoral member is received in a groove cut in the condyle of the femur, and its rear end face, constituting the inferior surface of the femoral member, bears against the upper surface of the tibial member. The inferior surface is arcuate polycentered in the sagittal plane and arcuate in the coronal plane. The superior surface of the femoral member has three different planar portions angularly disposed to one another, for load bearing purposes in three different angles of flexion of the knee.

10 Claims, 6 Drawing Figures

ARTIFICIAL KNEE JOINT

BACKGROUND OF THE INVENTION

This invention relates to an artificial knee prosthesis, for implantation by surgery into a knee joint as a partial replacement thereof.

The natural knee joint comprises the bottom part of the femur, constituted by the two condyles, the lower parts of the surfaces of which bear upon the complementary shaped upper surface plateaus of the tibia, through the intermediary of cartilage. Connection through the knee is provided by means of ligaments which also provide joint stability and help to absorb stresses applied to the knee. The femur, cartilage and tibia are are normally subjected to fairly heavy compression loading, being called upon to support substantial parts of the weight of the body.

Movement of the normal knee is a complex movement which includes rocking, gliding and axial rotation. Starting from the full extension position, the movement is also one of axial rotation of the femur about the tibia for about the first 10° of rotation. Then this motion converts to a rocking movement in which the femoral condyles roll posterially on the tibial plateaus. At about 20° of flexion, the type of movement changes again, to the gliding motion in which successive points on the femoral condyles slide forward on the tibial plateaus until full flexion is obtained.

The cartilage located between the femoral condyles and tibial plateaus effectively ensures free, smooth and painless flexion of the knee joint in the normal healthy knee. However, when the cartilage becomes damaged, diseased or inflamed, it ceases to function properly and flexion of the knee becomes difficult and painful. This is effectively what happens in various types of arthritis. To alleviate this condition, it is often necessary to remove the cartilage surgically, in whole or in part, with the result that the knee joint has no component or an inadequate component ensuring its free, smooth flexion.

BRIEF DESCRIPTION OF THE PRIOR ART

Previous proposals for artificial knee prothesis have been made, which include components for surgical implantation into a patient's knee. Due to the complex movement in the normal knee, however, the design of satisfactory artificial components which will permit such movement has proved difficult in practice. Components previously proposed have, in general, required substantial amounts of bone to be removed from the knee joint, by cutting, drilling and the like. This is undesirable, not only because it complicates and prolongs the required surgical procedures, but also because it reduces the amount of reserves of bone in the patient's knee which might at a later date be required to permit corrections of the installation to be made. Corrections are sometimes necessary after the prosthesis has been in place for substantial periods, due to wear of the components whilst in use. Prior art proposals have in general provided artificial knee prosthesis which are satisfactory over relatively short periods of use, but which develop problems on extended use, due to their particular design or arrangement of components.

SUMMARY OF THE INVENTION

It is an object of the present invention to provide a new and improved artificial knee prosthesis and components therefor, the surgical implantation.

It is a further object of the present invention to provide an artificial knee joint which will function satisfactorily for extended periods after implantation in the patient's knee, as a total or partial knee joint replacement.

The present invention provides an artificial knee prosthesis for insertion into a knee joint to assist in the provision of free, smooth flexion in the absence of the cartilage, or in the presence of a defective cartilage.

The present invention thus provides an artificial knee joint adapted for surgical insertion into a knee, comprising at least one artificial femoral member and at least one tibial member. The femoral member is of durable, rigid, smooth biocompatible first material, and has a rear portion with a rear end face which is arcuate polycentered in the sagittal plane and arcuate in the coronal plane, with respect to the direction in which it is installed in the knee. The front portion of the femoral member is generally planar and lies in the sagittal plane, having an indented front end face and being adapted to be received in a groove cut in the condyle of the femur of the knee so that the rear end face of the femoral member extends downwardly and constitutes the inferior surface thereof. The artificial tibial member is of plate-like form with a smooth shallow concave upper surface thereof being adapted to be received in the upper surface of the tibia bone of the knee, the second material being harder than the first material.

DESCRIPTION OF THE PREFERRED EMBODIMENTS

The first material comprising the femoral member according to the present invention is preferably a hard rigid plastic, such as high density polyethylene, polyester, nylon, polytetrafluoroethylene resin, or hard rigid silicone resin. Of these materials, high density polyethylene and polyester are preferred. These materials are readily available, relatively cheap, and inert and medically acceptable for prolonged contact with living organisms, readily shapable to the required shapes and configurations, and sufficiently strong, hard and rigid to allow their use over very extended periods of time. The upper surface of the tibial member is preferably of highly polished metal of a biocompatible type, e.g. stainless steel, cobalt-chromium alloy, titanium and its alloys. The provision of the femoral member of such hard plastic resin material to bear against a lower tibial member of metal is particularly advantageous, since such an arrangement provides contacting surfaces of very low coefficient of friction, and in use minimizes the rate of wear of the two components which contact each other, substantially reducing the likelihood of these parts requiring replacement on account of wear during the life of the patient.

The artificial knee joint of the present invention is thus of the unconstrained type, since it does not of itself include any connecting means such as hinges constraining the relative movement of the knee, but instead retains the original ligaments of the knee for connection between and control of the movements of the relative parts of the knee. It can thus be considered as a surface prosthesis.

Preferably, the rear portion of the femoral member according to the present invention has a greater width than the front portion, so that the rear portion overlies the front portion and the inferior surface is broader than the superior surface. The indented front end face is preferably perpendicular to the sides of the front portion, so as to present a superior surface of large area for load bearing purposes to the femoral condyle, consistent with the relative ease of installation. Such an arrangement minimizes the stresses of load bearing and reduces the tendency to split the femur when load is taken on the prosthesis. It will be appreciated that the terms front, rear, superior and inferior used in respect to the femoral member refer to positions of the various parts with reference to the knee joint after installation as hereinafter described.

Preferably also, the superior surface of the femoral member presents three different planar portions, angularly disposed relative to one another, and at different angles to the coronal plane. These planar portions take the load when the knee is at various positions. A first planar portion takes the load when the knee is at full extension, a second planar portion takes load when the knee is at an intermediate position between full flexion and full extension, and the third planar portion takes the load when the knee is at about 90° flexion.

In a preferred form, the front end face, or superior surface, which is to be received in a condyle is provided with a longitudinally extending groove, and a radio-opaque marker wire is provided in the central groove. The marker wire is suitably of metal, for example cobalt chromium alloy, stainless steel, titanium and its alloys. The marker wire is visible to x-rays, whereas the other parts of the femoral member are of plastic and are transparent to x-rays. The tibial member is of metal and is hence visible to x-rays. The provision of the marker wire on the femoral member enables the surgeon to check the artificial knee prosthesis periodically after surgical implantation thereof, by taking an x-ray picture of the rapaired knee. By measuring the distance between the marker wire and the tibial member, the surgeon can check for wear of the femoral member caused by use.

Also in the preferred embodiment, the femoral member is provided on its superior surface with a plurality of transversely extending grooves, which serve to assist in the anchoring of the femoral member firmly in the bone.

As previously noted, the tibial member is of the plate-like form. Its upper surface is shallow concave, and is adapted to receive thereon the arcuate inferior surface of the femoral member. The upper surface of the tibial member is of highly polished metal, so that the arcuate inferior surface of the femoral member may bear against it and allow relativey free rocking, gliding and axial relative movement between the members even under load. The lower surface of the tibial member is suitably of metal, and is preferably planar, roughened, so as to assist in the anchoring of the tibial member at the desired location on the tibia bone. In the alternative, the lower surface may be provided with projections, to assist in anchoring. The tibial member is installed at the edge of the tibial bone, so as to take advantage of the harder edge portions of the bone for supporting the tibial member, firmly and without subsequent sinking. The shape of the plate-like tibial member, as viewed in plan, is preferably generally appropriate for the overall shape of the knee joint, and has a generally semi-circular edge and a straight edge.

In some cases, it is necessary to repair a whole knee joint, removing all or substantially all of the cartilage from between the femur and the tibia. In such cases, i.e. a total knee replacement, two artificial femoral members are used, one secured in each condyle of the femur. Similarly, two artificial tibial members are used, secured to the top of the tibia in side-by-side relationship with their straight edges presented towards each other, so that each femoral member bears upon a separate tibial member. In other cases, it may be found by the surgeon that only a portion of the knee or cartilage is damaged, so that only half of the knee needs to be repaired. In such case, i.e. a half knee replacement, one femoral member is used, bearing against one appropriately positioned tibial member.

It will be appreciated that the femoral members and the tibial members according to the present invention can be made in a variety of different sizes, so as to offer to the surgeon a pair of prosthetic components generally appropriate for the size of the patient's knee requiring repair.

The femoral member and the tibial member are installed surgically in the knee, in using them to repair a knee joint. The knee is surgically opened and a groove is cut by means of surgical saws, drills and the like in the condyle of the femoral bones, to receive the femoral member projecting into the bone. The groove is made so that the generally planar front portion is a close fit in the groove, and the member is secured in place by application of bone cement. Similarly, a shallow groove is cut in the top of the tibia bone adjacent the edge of the bone with appropriate surgical cutting instruments, so that the tibial member is snugly received therein, with its lower surface presented downwardly into the bone. This may similarly be secured in place by means of bone cement, which is normally self-curing polymethylmethacrylate cement.

In the installation of the prosthesis of the present invention, the surgeon can make adjustments to the relative positions of the parts of the knee to correct various abnormalities, by varying the height on the tibia at which the tibial member is installed. Thus in a total or a half knee replacement, correct ligamentary lengths can be restored in the knee, by installing one or both tibial members so as to present the upper surface thereof at the correct height. Further in a total knee replacement, the relative heights of the upper surfaces of the two tibial members can be adjusted so as to correct misalignments of the original knee joint. By this means, varus (bow-legged) and vulgus (knock-kneed) deformities of up to 20° can be corrected.

In the most preferred embodiment of the invention, the rear end face constituting the inferior surface, of the femoral member is arcuate part circular in the coronal place. Such an arrangement allows for surgeon error in the surgical installation of the prosthesis, in that it is not essential that the groove cut in the femoral condyle to receive the femoral member be exactly in the sagittal plane. Nor is it necessary, in the case where a total knee replacement is undertaken, that the two femoral members be installed exactly parallel. The part circular configuration of the inferior surface allows for such small deviations from exact alignment. In a total knee replacement, the two femoral members should be aligned in the coronal plane, for fully correct installation.

The provision of an artificial knee joint according to the present invention, where the lower tibial member is of a relatively harder material than the upper femoral member, offers a number of significant and unexpected advantages. In use, the parts are sliding against one another every time the knee joint is moved, and often are called upon to bear a significant part of total body weight whilst they are sliding. Such sliding under load, over extended periods of time, will result in the relatively harder material forming microscopic pits and grooves in the softer material, and forming loose particles of softer material. An accumulation of such pits and particles in the vicinity of the relatively sliding parts will markedly increase the friction in the joint by effectively roughening the sliding surfaces. The present arrangement, with the harder material at the bottom, provides that the loose particles collect on the surface of the lower member and pitting of the surface of the lower member is avoided, so that the surface remains smooth, and loose particles are swept off this surface by repeated movements of the upper member sliding on the lower surface. If the arrangement of parts were reversed, the harder upper member would pit the upper surface of the lower member, loose particles would accumulate in and become embedded in such pits and grooved, rather than removed, and the surface would become roughened so that the friction in the knee joint would be increased to an undesirable extent.

Both the femoral member and the tibial member according to the present invention are designed so that they can be surgically installed with a minimum of bone removal, and the minimum cutting and drilling depth into the bones. Should the prosthesis fail to restore sufficient function or provide sufficient relief in any case, therefore, secondary surgical procedures are possible because adequate reserves of original bone remain.

BRIEF REFERENCE TO THE DRAWINGS

In the drawings, like reference numerals indicate like parts.

DETAILED DESCRIPTION OF THE MOST PREFERRED EMBODIMENT

Figure 1:
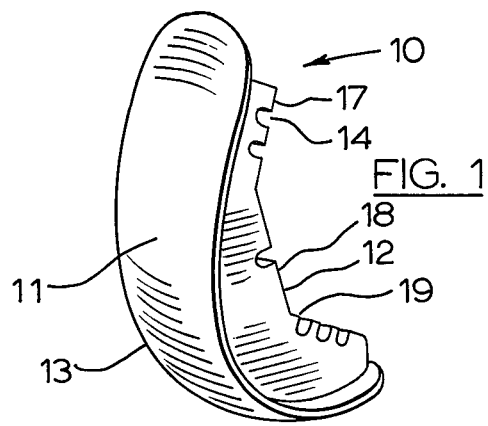
FIG. 1 is a perspective view of a femoral member constituting a part of a knee joint according to the present invention, generally from below.
Figure 2:
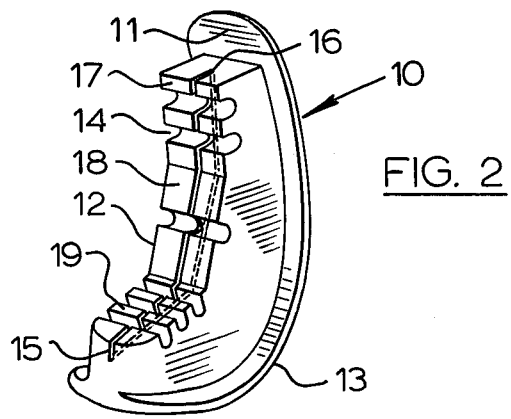
FIG. 2 is a perspective view of the femoral member of FIG. 1, generally from above.

With reference to FIGS. 1 and 2, the femoral member generally designated 10 consists of a rear portion 11 and a front portion 12, of generally planar form. The rear portion 11 has an arcuate rear end face 13, constituting the inferior surface of the femoral member. In the plane of the generally planar front portion 12, i.e. the sagittal plane as the prosthesis is installed, this end face 13 is arcuate polycentred. In the plane transverse thereto, the end face 13 is arcuate part circular substantially along the whole of its polycentred arcuate length.

The generally planar front portion 12 is integral with the rear portion 11, but of substantially less width, so that the rear portion 11 extends laterally beyond and overlies the front portion 12. The front portion 12 is provided on its front face, which constitutes the superior surface of the femoral member, with a series of transverse grooves such as 14 and a central longitudinal groove 15. A marker wire 16 of cobalt chrome is located at the bottom of the groove 15 and extends substantially along the bottom of the whole groove 15. The superior surface of the rear portion 12 at any particular point is planar. The superior surface has a first planar portion 17, a second planar portion 18 and a third planar portion 19, angularly disposed to one another, for load bearing purposes after installation in the knee.

Figure 3:
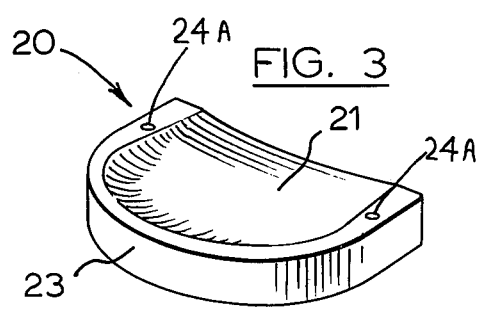
FIG. 3 is a perspective view of a tibial member constituting a part of a knee joint according to the present invention, generally from the top and front.
Figure 4:
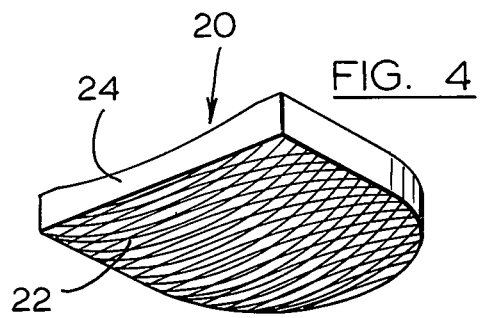
FIG. 4 is a perspective view of the tibial member of FIG. 3, generally from the bottom and rear.

With reference to FIGS. 3 and 4, the tibial member generally designated 20 is of generally plate-like form. The upper surface 21 thereof is shallow concave, whilst the lower surface 22 is planar. The tibial member 20 is made wholly of metal, with the upper surface 21 being highly polished and the lower surface 22 being roughened. One edge 23 is substantially semi-circular, and the other edge 24 straight, so as to be generally appropriate for the overall shape of the knee joint. Pits 24A are provided at the edges of the upper surface 21 to allow the tibial to be gripped by instruments during handling and installation. Corresponding pits, not illustrated, are provided on the lower surface 22.

Figure 5:
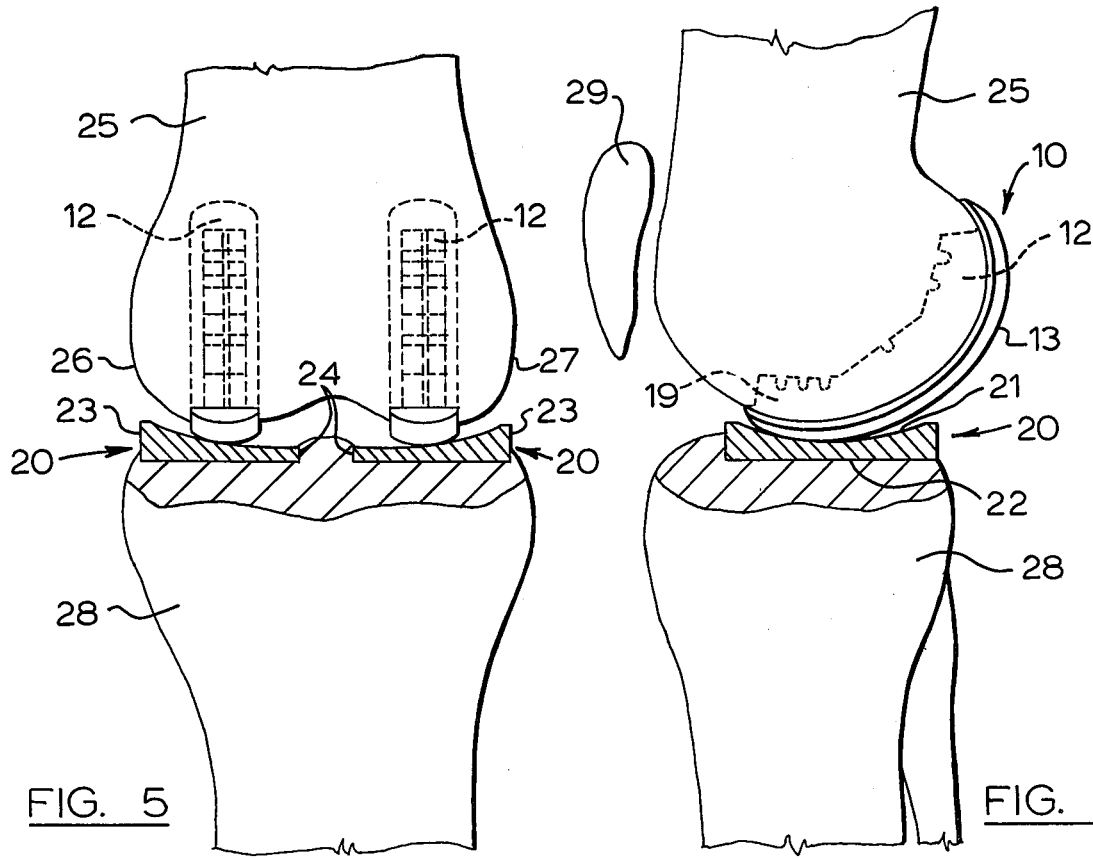
FIG. 5 is a diagrammatic front view, partly in section of a knee joint incorporating pairs of the components illustrated in FIGS. 1 - 4.
Figure 6:
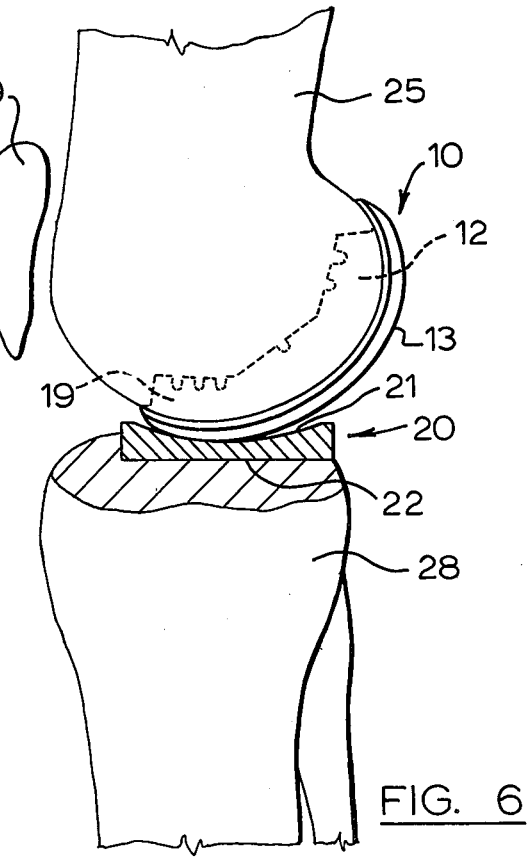
FIG. 6 is a diagrammatic side view, partly in section of the knee joint shown in FIG. 5.

FIGS. 5 and 6 illustrate diagrammatically a knee joint with pairs of femoral members 10 and tibial members 20 surgically implanted therein. The knee joint comprises the femur 25 terminating in condyles 26 and 27, the tibia 28 and the kneecap 29. The femoral members 10 are installed by cutting grooves in the condyles 26, 27 of the appropriate size to receive as a snug fit the generally planar front portions 12 of the femoral members 10. The inside surfaces of the rear portions 11 of the femoral members 10 rest upon and extend around the outer surfaces of the condyles 26, 27, so that the end faces 13 constitute the inferior surfaces of the femoral members and extend outwardly beyond the surfaces of the condyles 26, 27. The femoral members 10 are secured in place with bone cement in the transverse grooves 14 and along the front faces of the front portions 12. The marker wires 16 are placed in the longitudinal grooves 15 prior to surgical implantation of the femoral members 10.

The tibial members 20 are intalled by cutting shallow depressions of the appropriate size in the upper plateau of the tibia 28, so that they extend to the edge of the tibia 28. In the installation of a complete knee joint as illustrated, they are installed side-by-side. The upper concave surfaces 21 are presented upwardly, so as to receive thereon the arcuate rear end faces 13 constituting the inferior surfaces of the femoral member 10, which are substantially congruent with the surfaces 21. The tibial members 20 are secured in place by bone cement applied to the lower roughened surface 22 thereof. The tibial members 20 are installed with their semi-circular front edges 23 preferred outwardly, towards the side of the knee, and the straight edges 24 being presented toward each other.

As shown in FIG. 6, the knee joint with the femoral member 10 and the tibial member 20 intalled as described and illustrated can hinge in the vertical plane, the tibia 28 swinging to the right as shown in FIG. 6, with the end face 13 of femoral member 10 sliding on and bearing against the concave upper surface 21 of the tibial member 20. Substantially the same freedom of movement of the knee is thus afforded as with a natural knee joint. At full extension as shown, the planar surface 19 of femoral member 10 bears the load. At intermediate extension, planar surface 18 will move into a position to bear the load, and at 90° flexion planar surface 17 will move into a position to bear the load. The marker wire 16 and the tibial member 20 are both visible to x-rays, so that by measuring their relative positions from an x-ray picture, the surgeon can determine if either of the members has moved from its proper location, of if the femoral member 10 is experiencing significant amounts of wear, as the installed artificial knee joint of the invention is subjected to extended periods of use.

We claim:

1. An artificial knee joint adapted for surgical insertion into a knee, comprising at least one artificial femoral member of durable, rigid, smooth biocompatible material, the femoral member having a rear portion with a rear end face which is arcuate polycentred in the sagittal plane and arcuate in the coronal plane; and a front portion having front end face and being adapted to be received in a groove cut in the condyle of the femur of the knee so that said rear end face extends downwardly and constitutes the inferior surface of the femoral member and the front end face constitutes the superior surface of the femoral member, said superior surface presenting three different planar portions, angularly disposed relative to one another, and at different angles to the coronal plane; and at least one artificial tibial member of plate-like form with a smooth shallow concave upper surface of durable biocompatible material, the lower surface thereof being adapted to be received on the tibia bone of the knee.

2. The knee joint of claim 1, wherein the femoral member is of durable, rigid, smooth bicompatible first material, and the tibial member has an upper surface of durable, biocompatible second material, the second material being harder than the first material.

3. The knee joint of claim 2 wherein the first material is a hard rigid plastic, and the second material is a highly polished metal.

4. The knee joint of claim 3 wherein the first material is selected from the group consisting of high density polyethylene, polyester, nylon, polytetrafluoroethylene resin, and hard rigid silicone resin, and the second material is selected from the group consisting of stainless steel, cobalt-chromium alloys, titanium and titanium alloys.

5. The knee joint of claim 4 wherein the second material is stainless steel.

6. The knee joint of claim 3, wherein the rear end face of the femoral member constituting the inferior surface thereof is arcuate part-circular along the whole of its arcuate polycentred length, in a plane transverse to the sagittal plane.

7. The knee joint of claim 3, wherein the front face of the front portion of the femoral member constituting the superior surface thereof, is perpendicular to the sides of the front portion, so as to present a large surface area for load bearing purposes to the femoral condyle.

8. The knee joint of claim 3, wherein the superior surface of the femoral member is provided with a plurality of transversely extending grooves.

9. The knee joint of claim 3, wherein the superior surface of the femoral member is provided with a longitudinally extending central groove, and an x-ray visible marker wire of a material selected from the group consisting of cobalt-chromium alloy, stainless steel, titanium and titanium alloy is provided in the central groove.

10. The knee joint of claim 3, wherein the lower surface of the tibial member is roughened.

* * * * *